United States Patent
Dietz

[19]

[11] Patent Number: 6,126,660
[45] Date of Patent: Oct. 3, 2000

[54] SPINAL COMPRESSION AND DISTRACTION DEVICES AND SURGICAL METHODS

[75] Inventor: John W. Dietz, Indianapolis, Ind.

[73] Assignee: Sofamor Danek Holdings, Inc., Memphis, Tenn.

[21] Appl. No.: 09/124,343

[22] Filed: Jul. 29, 1998

[51] Int. Cl.[7] ................................................ A61B 17/56
[52] U.S. Cl. .............................................. 606/61; 623/17
[58] Field of Search ................................. 606/61, 62, 63, 606/59, 57, 105, 73; 623/17

[56] References Cited

U.S. PATENT DOCUMENTS

| | | |
|---|---|---|
| 3,731,673 | 5/1973 | Halloran . |
| 4,369,769 | 1/1983 | Edwards . |
| 4,386,603 | 6/1983 | Mayfield . |
| 4,422,451 | 12/1983 | Kalamchi . |
| 4,554,914 | 11/1985 | Kapp et al. ................................. 623/17 |
| 4,599,086 | 7/1986 | Doty . |
| 4,636,217 | 1/1987 | Ogilvie et al. ............................ 623/17 |
| 4,657,550 | 4/1987 | Daher . |
| 4,658,809 | 4/1987 | Ulrich et al. . |
| 4,854,304 | 8/1989 | Zielke . |
| 4,926,849 | 5/1990 | Downey . |
| 4,931,055 | 6/1990 | Bumpus et al. . |
| 5,000,163 | 3/1991 | Ray et al. . |
| 5,034,011 | 7/1991 | Howland . |
| 5,062,850 | 11/1991 | MacMillan et al. . |
| 5,108,395 | 4/1992 | Laurain . |
| 5,122,130 | 6/1992 | Keller . |
| 5,235,966 | 8/1993 | Jamner . |
| 5,290,312 | 3/1994 | Kojimoto et al. ......................... 606/61 |
| 5,391,180 | 2/1995 | Tovey et al. . |
| 5,396,880 | 3/1995 | Kagan et al. . |
| 5,403,276 | 4/1995 | Schechter et al. . |
| 5,439,464 | 8/1995 | Shapiro . |
| 5,443,515 | 8/1995 | Cohen et al. ............................. 606/61 |
| 5,512,038 | 4/1996 | O'Neal et al. . |
| 5,571,109 | 11/1996 | Bertagnoli . |
| 5,620,443 | 4/1997 | Gertzbein et al. . |
| 5,653,761 | 8/1997 | Pisharodi . |
| 5,697,889 | 12/1997 | Slotman et al. . |
| 5,700,291 | 12/1997 | Kuslich et al. . |
| 5,702,395 | 12/1997 | Hopf . |
| 5,702,453 | 12/1997 | Rabbe et al. . |
| 5,720,748 | 2/1998 | Kuslich et al. . |

OTHER PUBLICATIONS

Sofamor Danek Product Catalog, "Sofamor Danek The Spine Specialist," LIT–DCT–97, Sofamor Danek (Memphis, TN), entire catalog, dated 1997.

Laparoscopic Bone Dowel Surgical Technique, "Sofamor Danek The Spine Specialist," Lit.LBD.ST95, Sofamor Danek (Memphis, TN), 17 pages, dated 1995.

*Primary Examiner*—Michael Buiz
*Assistant Examiner*—Tan-Uyen T. Ho
*Attorney, Agent, or Firm*—Woodard, Emhardt, Naughton, Moriarty & McNett

[57] ABSTRACT

A spinal distraction device is provided that includes a body, a rack and a pinion-locking member. The body has a vertebral endplate engagement end and an opposite end. The body defines a chamber along its length and an opening at the opposite end in communication with the chamber. A gear bore is defined in communication with the chamber and has an axis perpendicular to the length. The rack is slidably disposed through the opening and within the chamber. The rack is slidable between a retracted position with the first end of the rack adjacent the vertebral engaging end of the body and the foot adjacent the opposite end of the body and a number of extended positions wherein the foot is at a distance from the opposite end of the body. The rack defines an engagement member with an engagement surface exposed to the gear bore. The pinion-locking member is rotatable within the gear bore to mesh with the engagement surface to convert rotary motion of the member to reciprocating motion of the rack. The member also includes a locking portion at one end of the member, which prevents rotation of the member within the gear bore. The member is slidable between a pinion position in which the pinion portion is disposed within the gear bore and a locked position in which the locking portion is disposed within the gear bore. The member is preferably biased to the locked position.

30 Claims, 9 Drawing Sheets

SPINAL COMPRESSION AND DISTRACTION DEVICES AND SURGICAL METHODS

FIELD OF THE INVENTION

The present invention relates to surgical methods and devices for the spine. Specifically, the invention concerns devices and procedures for stabilizing the spine during and after correction of injuries to or deformities of the spine.

BACKGROUND OF THE INVENTION

The upper lumbar and lower thoracic spine is the site of numerous spinal abnormalities and injuries. These may include trauma such as burst fractures, infection such as Pott's disease and other conditions such as tumors, post traumatic deformities, spinal cord compression, scoliosis and congenital deformities. Surgical approaches may be either posterior or anterior for many of these problems. In many cases the surgical approach is dictated by the pathology. In other cases, such as trauma to the thoracolumbar junction, the surgeon's preference and experience may allow either posterior or anterior approaches.

Anterior procedures at the thoracolumbar junction have traditionally been approached using one of several combined thoracic and retroperitoneal exposures. The classic approach usually involves a tenth rib thoracotomy. In this approach, an incision is made directly over the tenth rib and is carried caudally along the boarder of the rectus abdominus muscle. This is followed by excision of that rib and entry into the chest cavity. The lung is either packed away or deflated using a double lumen endotracheal tube. The diaphragm is taken down at its periphery to allow access to the retroperitoneal space which is then developed with blunt dissection. This technique was popularized by Hodgson and Stock and thoroughly described in *Moe's Textbook of Scoliosis*.

Other open approaches include extrapleural rib and flank approaches. In the eleventh rib approach, an incision over the eleventh rib is followed by a retropleural approach to the spine. This approach spares the chest cavity from invasion. The twelfth rib approach is very similar. The twelfth rib is removed followed by a retroperitoneal exposure of the spine. Similarly, the flank approach may be used to expose the retroperitoneal space and then extend cephalad under the diaphragm. Each of these approaches may be chosen for its utility in achieving exposure for the patient's particular problem, the specific spinal levels to be operated and the surgeon's experience.

Following these various surgical approaches, numerous anterior systems have been employed including dual rod systems and plate systems such as disclosed in U.S. Pat. Nos. 5,108,395 and 5,702,395. These instrumentation systems rely on reconstituting the load bearing function of the anterior column by insertion of a bone graft or cage spanning a fractured segment after removing the fractured vertebra and the adjacent two discs. Stability is achieved typically with two screws in adjacent vertebra spanned by a longitudinal plate or two rods. The advantages of the anterior approach include restoration of anterior load bearing capability at the time of surgery and fusion of only the levels adjacent to the incompetent vertebra.

Each of the open approaches require significant exposure of several levels of the spine, causing a great degree of approach related morbidity. The degree of morbidity increases as the number of exposed spinal levels expands. Morbidity includes post operative incision pain, pain associated with rib removal, risks to the intercostal vessels and intercostal neuritis. Substantially longer scars also cause concern for cosmesis in some patients.

Spinal conditions have also been treated posteriorly with Harrington distraction instrumentation. The Harrington instrumentation includes hooks and rods to effect and maintain corrected positioning of vertebrae during the fusion process. The rods are used to apply forces to straighten the spine and to maintain the corrected configuration until the vertebrae are fused. Typically, fusion is attempted from several levels above the pathology site to several levels below. The exact number of levels fused depends on the character of the fracture and the surgeon's training and varies from three to six vertebra. When following a "rod long, fuse short" philosophy, many surgeons have recommended removing the rods after the fusion has healed. Harrington type instrumentation is disclosed in U.S. Pat. Nos. 4,369,769 and 4,386,603, for example.

Many surgeons debate the biomechanical and clinical advantages and disadvantages of posterior versus anterior treatment of fractures and other conditions. One reason anterior approaches may be preferred is that they allow surgeons to address thoracolumbar fractures directly at the site of greatest biomechanical advantage. First, the material causing the injury usually lies anteriorly and is therefore most easily removed from this aspect. Also, the motor tracts lie predominantly on the anterior aspect of the spinal cord and may more easily be restored from this approach. Finally, it is generally agreed that decompression of the neural tissue to facilitate a patient's recovery from acute traumatic spinal cord injuries is best accomplished through an anterior approach to the spine.

The anterior approach would provide a clear advantage if approach related morbidity from the anterior approach to the thoracolumbar spine could be reduced through minimally invasive endoscopic techniques. An endoscopic approach to the thoracolumbar junction would also allow minimally invasive access for other procedures such as anterior releases for scoliosis, anterior instrumentation for scoliosis, spinal cord decompression for tumor or infection, biopsies, and repair of post traumatic kyphosis.

In spite of the potential benefits of such endoscopic techniques, challenges remain. In many cases, distraction or compression is required to correctly reposition the spinal deformity after the spinal cord has been decompressed. Typically, portions of the anterior vertebral column (i.e., the vertebral body) are removed to relieve pressure on the anterior portion of the spinal cord. Bone grafting and fusion is then required to achieve a stable correction. These requirements have not lent themselves to the confines of an endoscopic approach using prior art technology. Therefore, a need has remained for endoscopic devices and techniques for curvature correction, spinal canal decompression, anterior fusion, and internal fixation.

SUMMARY OF THE INVENTION

Briefly describing one aspect of the invention, a spinal distraction device is provided that includes a body, a rack and a pinion-locking member for moving the rack and maintaining it in various positions relative to the body. The body has a vertebral endplate engagement end and an opposite end. The body defines a chamber along its length and an opening at both ends in communication with the chamber. A gear bore is defined at a location along the length. The gear bore is in communication with the chamber and has an axis perpendicular to the length.

The rack is slidably disposed through the opening and within the chamber. A rack has a first end, a second end and a foot projecting transversely from the first end. The foot has a vertebral engaging surface. The rack is slidable between a retracted position with the first end of the rack adjacent the vertebral engaging end of the body and the foot adjacent the opposite end of the body and a number of extended positions wherein the foot is at a distance from the opposite end of the body. The rack also defines an engagement member between the first end and the second end. The engagement member defines an engagement surface exposed to the gear bore.

The pinion-locking member is rotatably and slidably disposed within the gear bore. The member includes a pinion portion and a locking portion. The pinion portion defines a pinion surface complementary to the engagement surface of the rack. The member is rotatable within the gear bore so that the pinion surface can mesh with the engagement surface of the rack to convert rotary motion of the member to reciprocating motion of the rack. The locking portion is disposed at an end of the member and prevents rotation of the member within the gear bore. The member is slidable between a pinion position in which the pinion portion is disposed within the gear bore and a locked position in which the locking portion is disposed within the gear bore. In preferred embodiments, a spring is disposed within the gear bore and biases the member toward the locked position. The bias can be overcome by pressure on the endcap that pushes the member in to the pinion position.

In another embodiment, the invention includes an endoscopic spinal distraction assembly. The assembly includes a cannula positionable through a portal in a patient's tissue from the skin to the pathology site. The cannula defines a passageway therethrough along its length. A distraction device is also provided. The device includes a pair of vertebral body engaging members on opposite ends of the device. The device is slidable between a retracted position and an extended position. The device is dimensioned in the retracted position for delivery through the passageway to the pathology site. An insertion driver for delivering the device to the pathology site. The driver includes a hollow outer shaft dimensioned to be inserted through the passageway of the cannula, holding means for holding the distraction device for delivery through the cannula and a driver mechanism slidably engaged within the outer shaft for operationally engaging the driver.

The invention also provides an endoscopic method for stabilizing a spine in a patient. This method comprises the steps of 1) approaching a site of pathology on the spine through a cannula defining a passageway through the patient's skin and tissue to the spine; 2) excising a vertebral disc at the site through the passageway; 3) removing a vertebral body at the site through the passageway to leave a space between the endplates of the bodies of two adjacent vertebrae; 4) inserting a distraction device through the passageway and into the space, the distraction device having a pair of vertebral body engaging members on opposite ends of the distraction device, the distraction device slidable between a retracted position and an extended position; 5) positioning the device in the retracted position within the space to orient the engaging members to contact the endplates of the adjacent vertebrae; 6) sliding the device from the retracted position to the extended position to increase the space between the adjacent vertebrae to obtain a distracted space having a distraction distance; 7) providing a fusion spacer corresponding to the distraction distance; 8) inserting the fusion spacer into the distraction space; and 9) removing the distraction device leaving the fusion spacer in the distracted space.

Accordingly, it is one object of the invention to provide endoscopic spinal distraction devices and methods. This and other objects, advantages and features are accomplished according to the devices and methods of the present invention.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

The present invention provides methods, instrumentation and devices for endoscopically approaching and stabilizing the spine. Devices are provided for distraction and compression. The distraction devices have a pair of vertebral body engaging members on opposite ends of the distraction device. The device is slidable between a retracted position, for insertion through a cannula and into an intervertebral space, and extended positions in which the engaging members impart a force on the vertebra for distraction.

Figure 1:
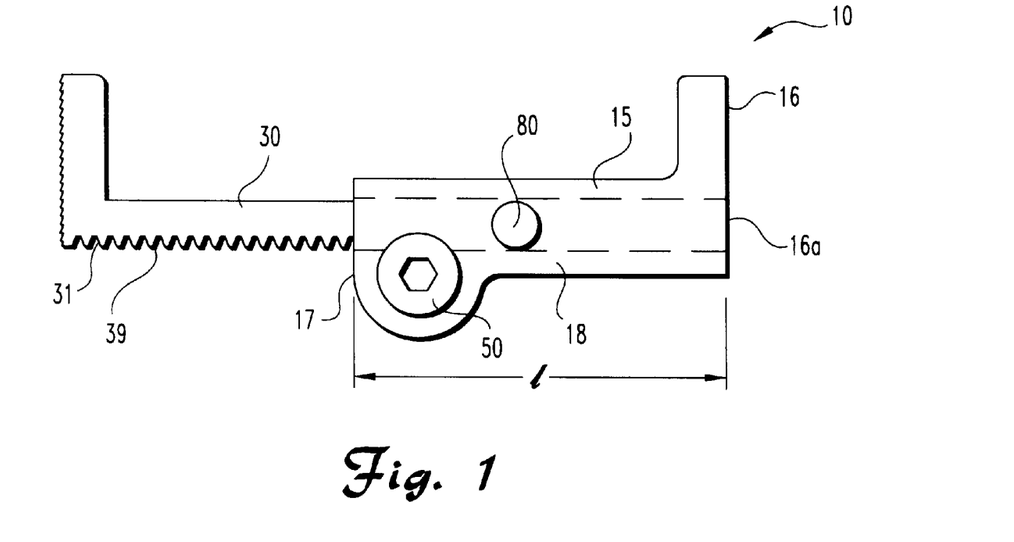
FIG. 1 is a front elevational view of a device according to this invention.
Figure 2:
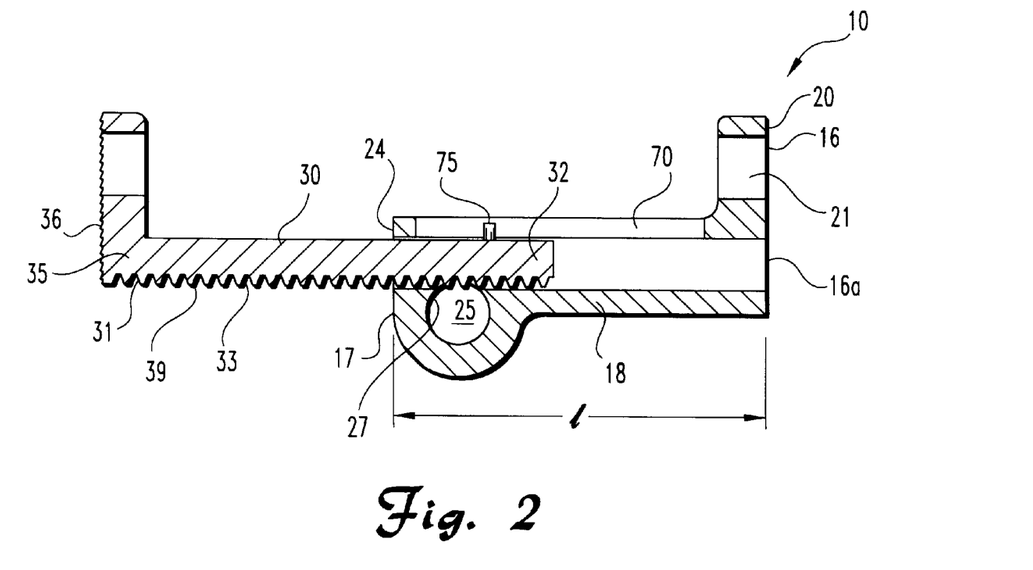
FIG. 2 is a sectional view of the device shown in FIG. 1 in an extended position.
Figure 3:
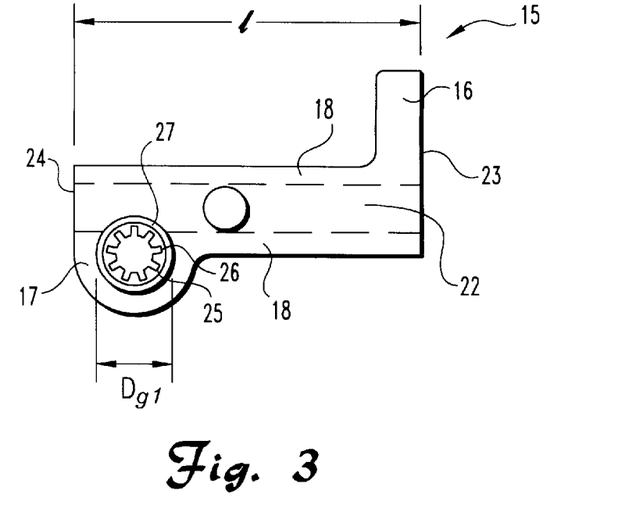
FIG. 3 is a front elevational view of the body of the device shown in FIG. 1.
Figure 4:
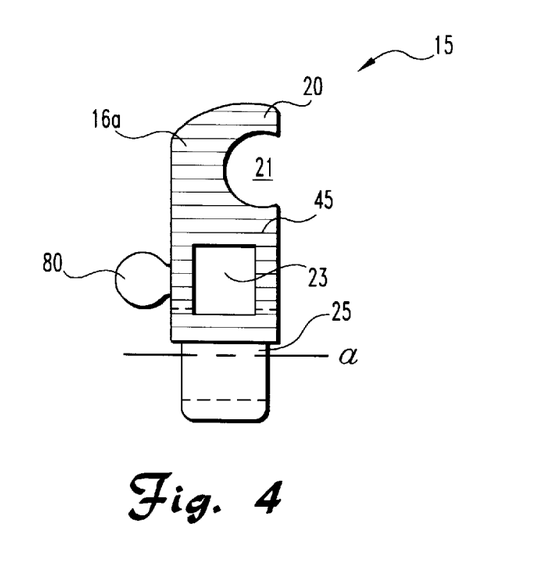
FIG. 4 is an end elevational view of the body of the device shown in FIG. 1.
Figure 5:
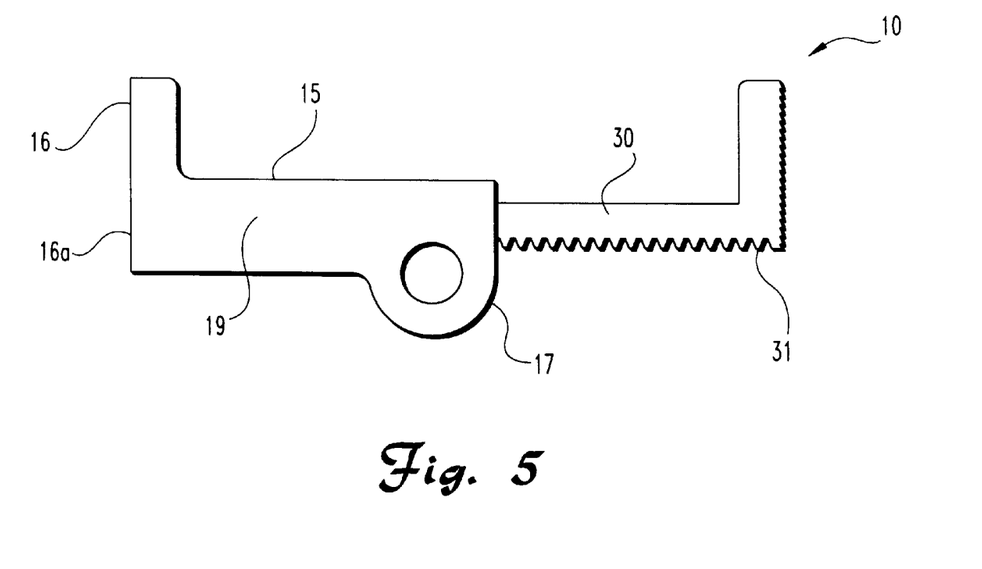
FIG. 5 is a back elevational view of the device shown in FIG. 1.
Figure 6:
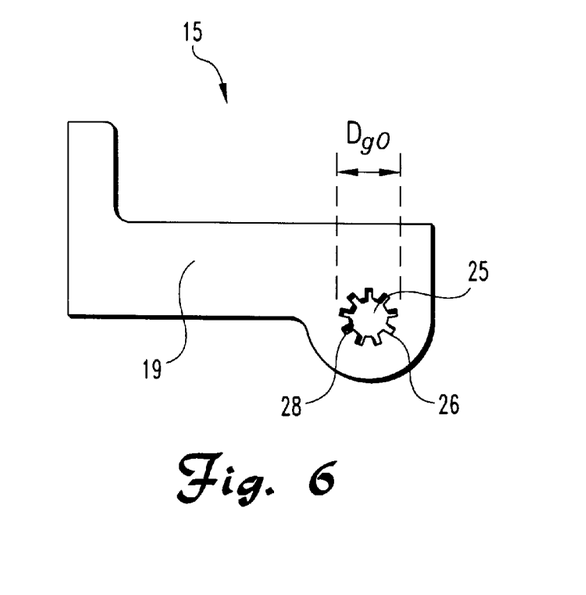
FIG. 6 is a back elevational view of the body of the device shown in FIG. 1.

An endoscopic spinal distraction device 10 in accordance with a preferred embodiment of the invention is depicted in FIGS. 1–6. The device 10 includes a body 15 having a vertebral endplate engagement end 16, an opposite end 17 and a length l between the engagement end 16 and the opposite end 17, respectively. The body 15 defines a chamber 22 (FIG. 2) along the length l and openings 23, 24 (FIG. 3) at the engagement end 16 and the opposite end 17, respectively. The openings 23, 24 are in communication with the chamber 22. The body 15 also defines a gear bore 25 at a location alone its length l. The gear bore 25 is also in communication with the chamber 22 and has an axis perpendicular to the length l as shown in FIG. 4. The gear bore 25 is preferably defined through the body 15 from the first side 18 to the opposite side 19 of the body 15. As shown in FIGS. 3 and 6, the gear bore 25 terminates at the first gear opening 27 at the first side 18 of the body 15 and the opposite gear opening 28 at the opposite side 19 of the body 15.

Figure 7:
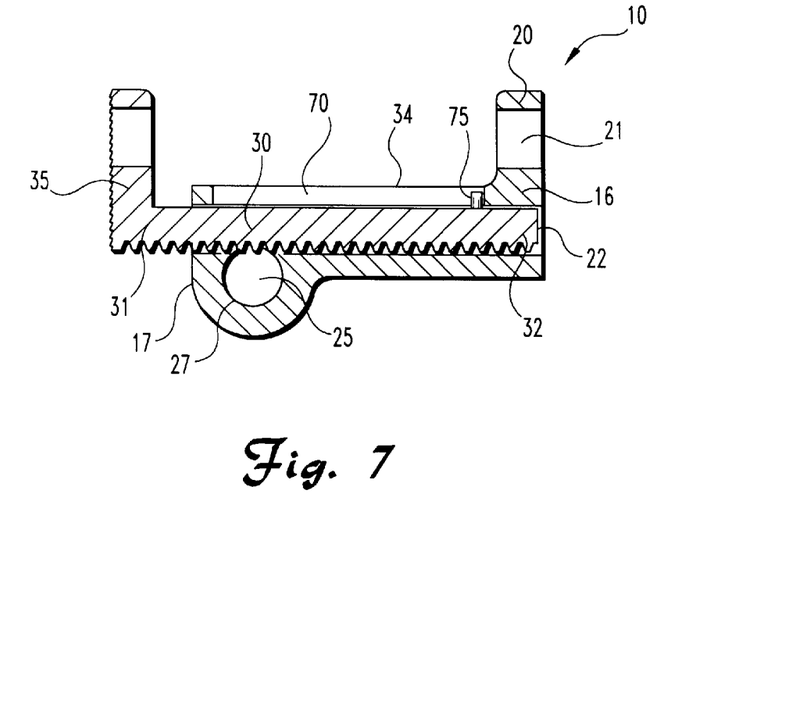
FIG. 7 is a sectional view of the device shown in FIG. 1 in a retracted position.
Figure 8:
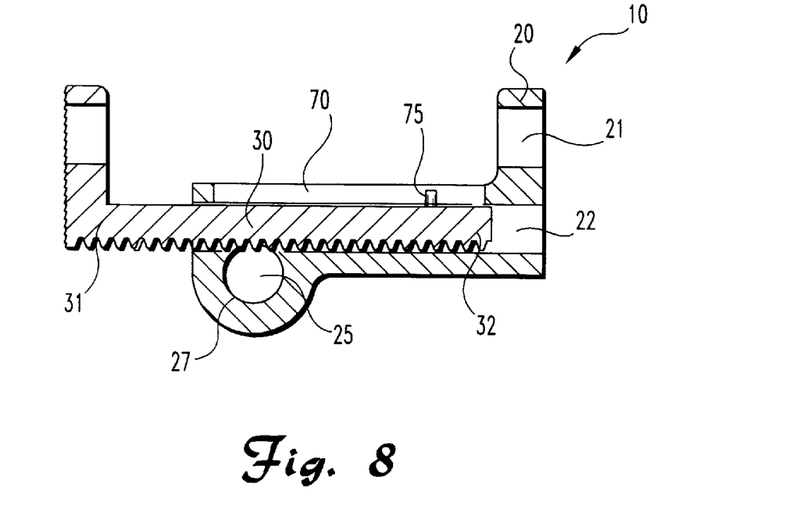
FIG. 8 is a sectional view of the device shown in FIG. 1 in a partially extended position.

Referring again to FIG. 2, the device 10 includes a rack 30 slidably disposed through the second opening 24 and within the chamber 22. Rack 30 has a first end 31 and a second end 32. A foot 35 with a vertebral endplate engaging surface 36 projects transversely from the first end 31. Rack 30 is slidable between a retracted position as shown in FIG. 7 and a number of extended positions. FIG. 2 shows rack 30 in a fully extended position. Device 10 can also assume various intermediate positions between the retracted and fully extended positions. One such intermediate position is shown in FIG. 8. Referring again to FIG. 7, in the retracted position, the second end 32 of rack 30 is adjacent the endplate engagement end 16 of the body 15 and the foot 35 is adjacent the opposite end 17 of the body 15. In the extended positions foot 35 is disposed at a surgeon definable distance from the opposite end 17 of body 15. This distance can be established based on the anatomy of the instrumented vertebral level.

Figure 9:
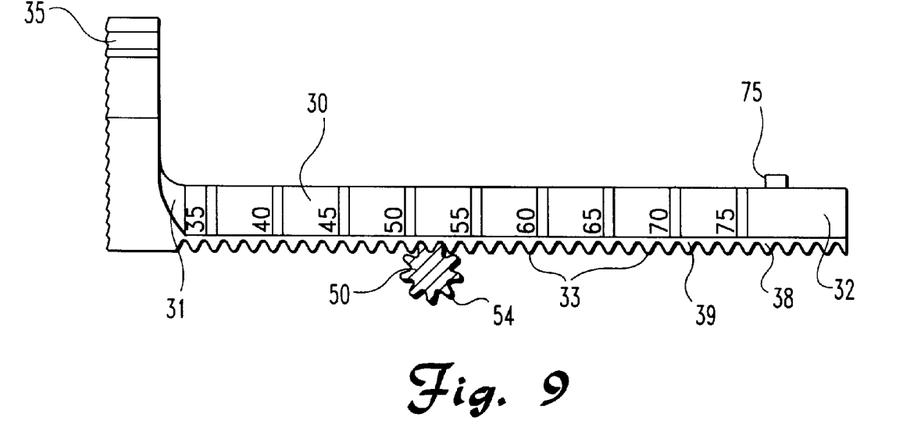
FIG. 9 is a side elevational view of a rack engaged to a pinion according to this invention.

Rack 30 defines an engagement element 38 between the first end 31 and the second end 32 as shown more clearly in FIG. 9. The engagement element 38 further defines an engagement surface 39 exposed to the gear bore 25 of body 15 when rack 30 is disposed within chamber 22. In a preferred embodiment, the engagement surface 39 includes a number of spaced apart teeth 33.

Figure 10:
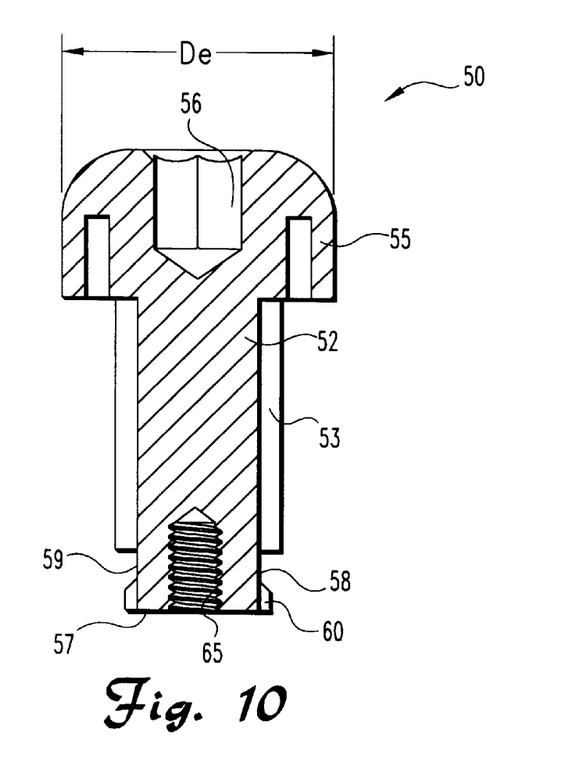
FIG. 10 is a sectional view of a pinion-locking member of the device shown in FIG. 1.

Referring now to FIGS. 1 and 10, the device 10 also includes a pinion-locking member 50 rotatably and slidably disposed within the gear bore 25. The member 50 includes a pinion portion 52 and a locking portion 58 that each cooperate with the body 15 and the rack 30 to move the rack 30 between the retracted and extended positions and then lock the device 10 in a desired position. The member 50 is slidable between a pinion position shown in FIG. 11 and a locked position shown in FIG. 12. In the pinion position, the pinion portion 52 is disposed within the gear bore 25 so that the pinion teeth 33 of rack 30 are in position to engage rack teeth 33 to move the rack 30 within chamber 22. In the locked position, the locking portion 58 is disposed within the gear bore 25 to prevent rotation of the member 50 and thus movement of the rack 30.

The pinion surface 53 is complementary to the engagement surface 39 of rack 30. In a preferred embodiment, the pinion surface 53 defines pinion teeth 54 for meshing with the spaced apart teeth 33 of the rack 30 as most clearly shown in FIG. 9. As the pinion portion 52 rotates within the gear bore 25, teeth 54 mesh with the engagement surface 39 of the rack 30 to convert rotary motion of the member 50 to reciprocating motion of rack 30. Thus, rotation of the pinion member 50 within the gear bore 25 moves the rack 30 between the retracted and extended positions.

Referring again to FIGS. 3 and 10, the pinion-locking member 50 preferably includes an end cap 55 adjacent and attached to the pinion portion 52. End cap 55 has an outer dimension $D_e$ larger than a dimension $D_{gi}$ of the first gear opening 27. Preferably, the end cap 55 includes a tool engaging member 56 for providing a rotational force to the pinion-locking member 50. In the embodiment shown in FIG. 10, the tool engaging member 56 is an internal hex for receiving a hex driver.

Preferably, a locking portion 58 is provided at an end 57 of the member 50. The locking portion 58 includes means for blocking undesired rotation of the member 50 within the gear bore 25 to prevent movement of the rack 30. In a preferred embodiment, the means includes a number of locking teeth 60 along an outer surface 59 of the locking portion 58. Referring now to FIG. 6, the body 15 preferably defines a locking groove 26 at one portion of the gear bore 25, with a locking groove 26 defined for each locking tooth 60. In this preferred embodiment, each groove is sized and shaped to engage one of the locking teeth 60 to prevent rotation of the pinion-locking member 50 when the member 50 is in the locked position shown in FIG. 12. Preferably, the opposite side 19 of the body 15 defines the grooves 26 circumscribing the opposite opening 29. It is understood that other mating locking configuration between portion 58 and groove 26 are also contemplated.

Figure 11:
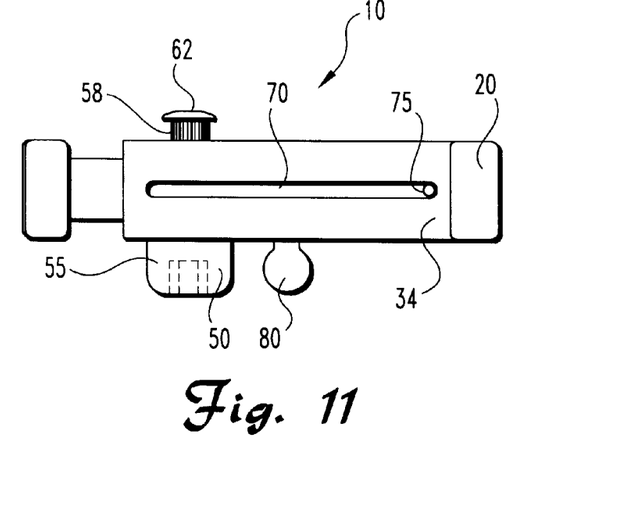
FIG. 11 is a top elevational view of the device shown in FIG. 1 with the pinion-locking member in the pinion position.
Figure 12:
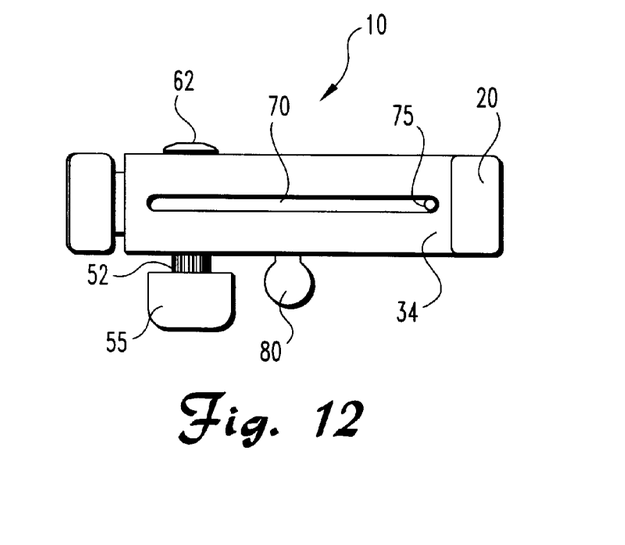
FIG. 12 is a top elevational view of the device shown in FIG. 1 with the pinion-locking member in the locked position.
Figure 13:
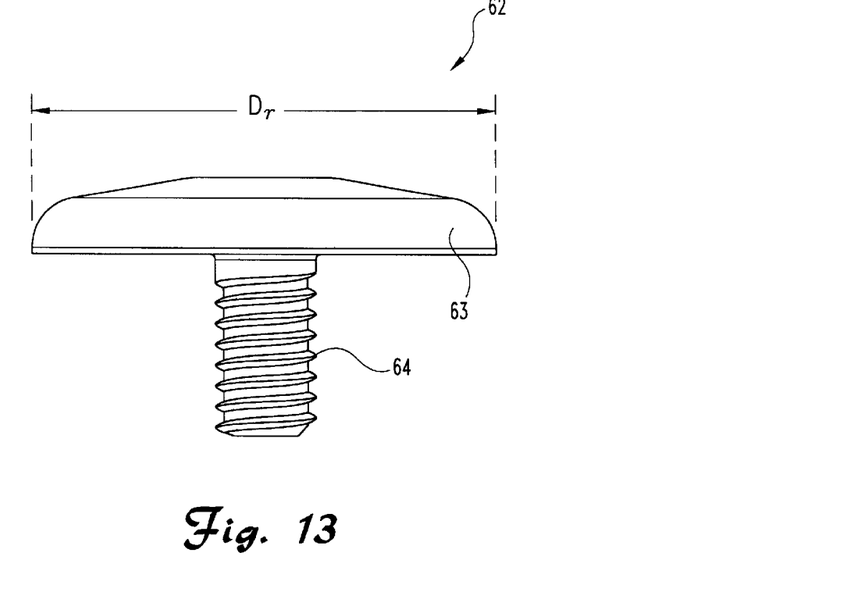
FIG. 13 is a side elevational view of a retainer of this invention.

In preferred embodiments, the pinion-locking member 50 includes a retainer 62 attached to the locking portion 58 as shown in FIGS. 11 and 13. The retainer 62 has an enlarged head 63 and a stem 64. The head 63 has an outer dimension $D_r$ larger than a dimension $D_{go}$ (FIG. 6) of the opposite gear opening 28. Preferably, stem 64 defines engaging means for engaging the retainer 62 to the pinion-locking member 50. Any suitable means is contemplated. For example, the stud 64 may be threaded to engage an internally threaded pin hole 65 in the member 50.

Figure 14:
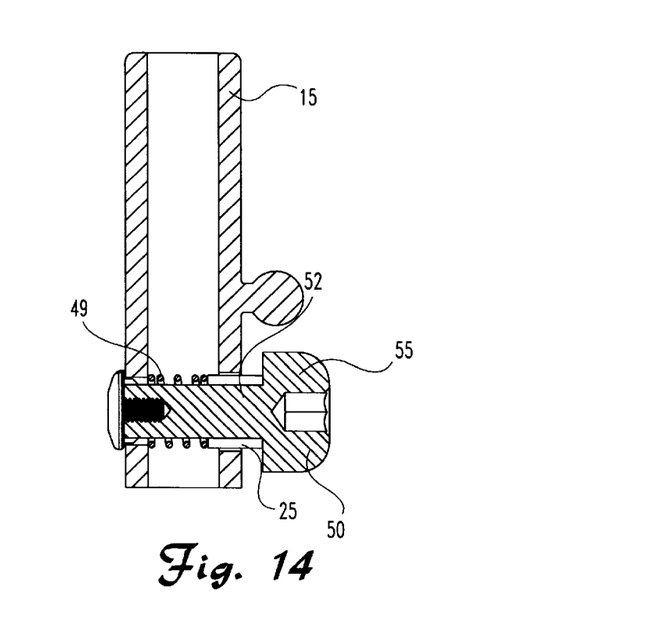
FIG. 14 is a sectional view of a device of this invention with the pinion-locking member spring biased into a locked position.
Figure 15:
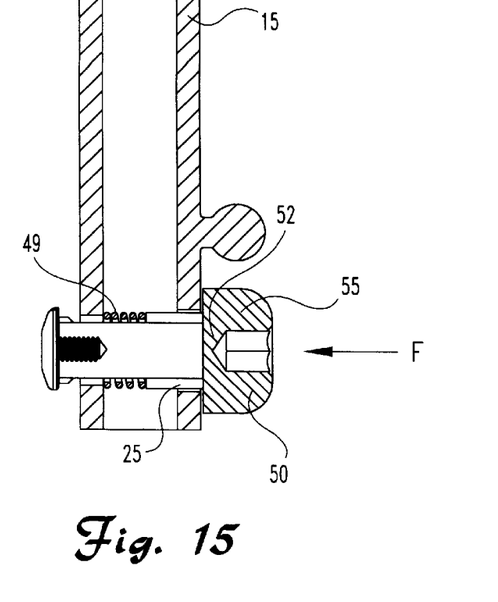
FIG. 15 is a sectional view of the device depicted in FIG. 14 with the pinion-locking member in the pinion position.

Referring now to FIG. 14, device 10 preferably includes a spring 49 disposed in the gear bore 25 and biasing the pinion-locking member 50 toward the locked position. Spring 49 maintains rack 30 in a particular position with respect to body 15. The bias can be overcome by the application of a force F on the end cap 55. Force F pushes the member 50 into the pinion position with the pinion portion 52 disposed within the gear bore 25 and compresses spring 49 as shown in FIG. 15. During the application of force F, member 50 can be rotated to translate rack 30 for distraction. When the force F is removed, spring 49 returns to its initial position shown in FIG. 14 and the pinion-locking member 50 returns to its locked position with the rack 30 at a desired extended position.

Because one use of the device 10 is placement between adjacent vertebra for distracting the vertebra, it is preferred that the foot 35 and the vertebral engagement end 16 of the body 15 each define a vertebral endplate engaging surface 16a, 36. In a preferred embodiment depicted in FIGS. 4 and 16, the surfaces 16a, 36 each define a number of ridges 45 for biting into the endplates of the vertebra to provide stability as the distraction force is imparted to the vertebra.

The device 10 can also include limiting means for limiting the translation of the rack 30 within the chamber 22. Rack 30 is slidable within the chamber 22 between two end points: the fully retracted position shown in FIG. 7 and the fully extended position shown in FIG. 2. In one embodiment most clearly shown in FIG. 12, the limiting means includes a channel 70 defined in the outer surface 34 along a portion of the length l of the body 15. Channel 70 is in communication with the chamber 22 and rack 30 includes a pin 75 slidably disposed within the channel 70.

In some embodiments, the device 10 also includes a projection 80 extending from the body 15, which aids in the positioning of the device 10 through a cannula 100 and within an intervertebral space. Projection 80 is sized and shaped for grasping to position the body 15. As shown in FIG. 1, the projection 80 can extend from the first side 18 of the body 15.

The invention includes several features that enhance the endoscopic capabilities of the device 10. For example, the outer surface 34 of the rack 30 shown in FIG. 9 includes ruled indicia for measuring a distance between the foot 35 and the opposite end 17 of the body 15 when the rack 30 is in one of the extended positions. This provides a visual measure of the distraction distance that can be viewed through the endoscope. A bone graft or fusion device of appropriate height can then be selected and placed into the distracted space before the device is removed.

Figure 16:
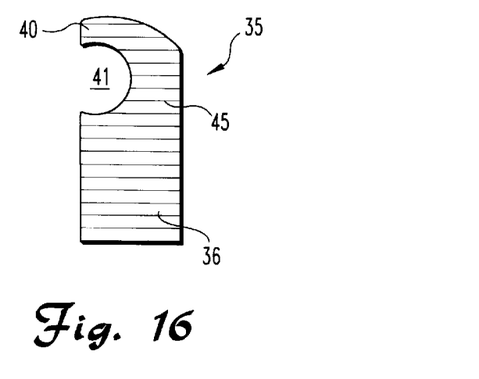
FIG. 16 is an end elevational view of the rack of the device shown in FIG. 1.

In some embodiments, the device 10 can also be used for compression. In such embodiments, the vertebral engagement end 16 of the body 15 and the foot 35 of the rack 30 each terminate in a hook 20, 40 as shown in FIGS. 4 and 16. Each of the hooks 20, 40 define a cavity 21, 41 for receiving a spinal rod. The cavities may either both open to the opposite side or the first side of the body 15. In this embodiment, a fastener, such as an eyebolt, can engage the rod to fix the position of each hook 20, 40. Distraction can be accomplished by contacting each eyebolt with a distractor spreader, loosening the eyebolts, pushing the eyebolts and then re-tightening onto the rod.

Figure 17:
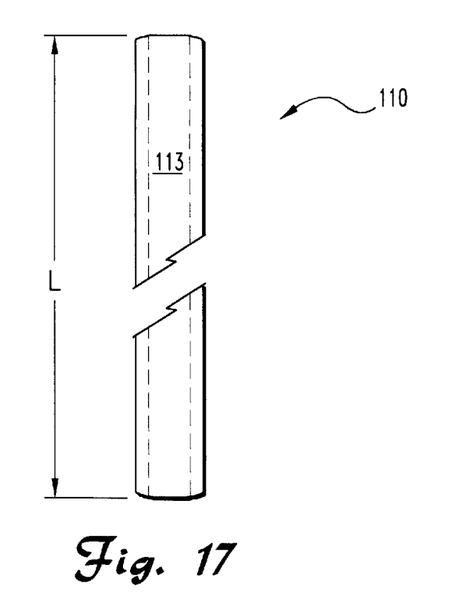
FIG. 17 is a partial side elevational view of an endoscope according to this invention.
Figure 18:
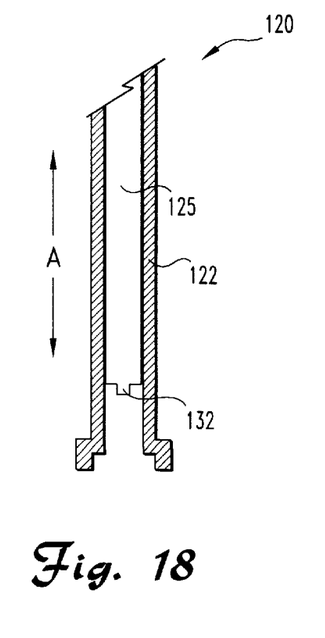
FIG. 18 is a side sectional view of another embodiment of an insertion driver of this invention.
Figure 19:
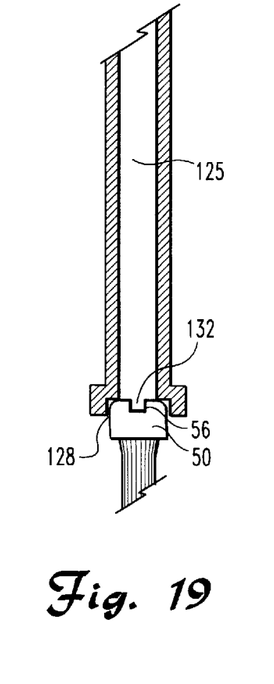
FIG. 19 is a side sectional view of a driver of this invention engaged to a distraction device.

The invention also includes an endoscopic spinal stabilization assembly. The assembly includes a cannula 110 positionable through a portal in a patient's tissue from the patient's skin to a pathology site in the patient's spine. The cannula 110 has a length L and defines a passageway therethrough along the length L as shown in FIG. 17. The assembly also preferably includes an insertion driver 120 for delivering a device to the pathology site. The insertion driver shown in FIG. 18 includes a hollow outer shaft 122 dimensioned to be inserted through the passageway 113 of the cannula 110 and a driver mechanism 125 slidably engaged within the outer shaft 122 for operationally engaging the device. The driver mechanism 125 is slidable within the outer shaft 122 in the direction of the arrow A. An engagement member is provided at one end of the driver mechanism 125 for engaging a tool engaging member 56 of a device 10. For example, the driver mechanism 125 in a preferred embodiment includes a hex 132 for engaging the internal hex 56 of pinion-locking member 50 as shown in FIG. 19. When a spring biased pinion-locking member is used, the driver mechanism 125 can be used to apply force F on the member 50 to push the member 50 into the pinion position as in FIG. 15.

The driver 120 also preferably includes holding means for holding the device for delivery through the cannula 110. The holding means of the driver 120 of FIG. 19 includes a collar 127 defining a receptacle 128 sized to snugly receive a portion of the device 10, such as the pinion-locking member 50. In another embodiment, depicted in FIG. 18, the holding means includes a pair of prongs 129 extending from the end of the outer shaft 122. In some embodiments, the holding means also facilitates movement of the rack 30 of the device 10. For example, the outer shaft 122 can be rotated to turn the pinion-locking member 50.

The assembly can also include other devices and instruments useful for endoscopic spinal surgery such as a long handled ball tip probe and a long handled tap. The probe and tap preferably have millimeter markers along their shafts that facilitate measurement through the cannula 110.

The present invention also provides endoscopic methods for stabilizing a spine in a patient. The methods include approaching a site of pathology on the spine through a cannula defining a passageway through the patient's skin and tissue to the spine. The vertebral disc at the site is excised and the vertebral body is removed through the passageway to leave a space between the endplates of the bodies of two adjacent vertebrae. A distraction device is then inserted through the passageway and into the space. The device is placed in the retracted position within the space and the device 10 is oriented so that the engaging members contact the endplates of the adjacent vertebrae. The device is then slid from the retracted position to the extended position to increase the space between the adjacent vertebrae to obtain a distracted space having a distraction distance. A fusion spacer corresponding to the distraction distance is then inserted into the distraction space. The distraction device is then removed leaving the fusion spacer in the distracted space.

The present invention shall be more concretely explained with the following examples, which are considered to be merely representative of the present invention and thus should not be considered as limiting.

EXAMPLES

This study sought to develop techniques allowing lateral exposure from the upper thoracic spine to the lateral aspect of L5 under one anesthetic and without repositioning the patient, with particular interest to fully exposing the thoracolumbar junction for the spinal canal decompression and anterior fusion.

Endoscopic Retroperitoneal Thoraco-Abdominal
Approach to the Upper Lumbar Spine

This study consisted of two parts. The approach was developed in the laboratory using a live porcine preparation used extensively to train endoscopic surgeons in our area. The technique was then applied in the operating room with selected clinical problems.

Porcine Model

The laboratory model consisted of 27 porcine preparations over a 16-month period. Initially, we used various techniques and types of equipment to develop expertise in the approach. These included thoracoscopy, intra peritoneal exposures, retroperitoneal exposures and combination exposures. Vertebrectomy and spinal canal decompression was then added. Finally, instrumentation across a vertebrectomy was included.

Five pigs were prepared to test whether endoscopic retroperitoneal thoraco-abdominal exposure with vertebrectomy and strut graft could be accomplished without causing catastrophic spinal cord damage. The exposure was accomplished as described below. A complete excision of the L1 vertebral body was performed and a strut graft of poly methyl methacrylate was placed between T12 and L2. At the conclusion of the procedure the pig was euthenized and open exposure used to observe for graft placement and evidence of injury to the neural structures. In one pig, appropriate anesthesia and analgesia was employed to allow observation spontaneous lower extremity motor function post operatively. The pig was then euthenized and open exposure used to verify graft position. In these five procedures graft position was appropriate and there was no evidence of neural injury.

HUMAN SURGICAL TECHNIQUE

Six patients were treated using the methods and devices of this invention. Table 1 describes the patients.

TABLE 1

Patient Profiles

| Patient Number | Age | Levels Exposed | Diagnosis |
| --- | --- | --- | --- |
| 1 | 20 | L1–L4 | Post traumatic kyphosis |
| 2 | 63 | T12 to L2 | L1 burst fracture with incomplete spinal cord injury |
| 3 | 36 | T11–T12 | Trauma with neural compromise |
| 4 | 16 | T7 to L3 | Kyphoscoliosis |
| 5 | 16 | T12 to L3 | Idiopathic scoliosis |
| 6 | 13 | T4 to L3 | Neuromuscular scoliosis |

Preparation

In each case, the patient was placed in the lateral position with the left side up unless the spinal deformity or pathology indicated that a right-sided approach would be advantageous. Great care was taken to position the patient vertically so that a vertical radiograph would be a perfect lateral examination. A bump was placed under the waist to level the spine if necessary so that a horizontal radiograph would be a perfect antero-posterior examination. Next, fluoroscopy was used to identify the site of pathology and choose portal sites. Generally, four portals were used. The first working portal was placed directly over the site of pathology in the anterior axillary line. The second and third working portals were placed directly over the adjacent vertebral bodies in the mid axillary line. The caudal portal was placed in the anterior axillary line two or three segments below the site of pathology.

Dissection

An endoscopic retroperitoneal dissection was performed first. The caudal portal was created and the retroperitoneal space identified with blunt dissection by the surgeon's fingertip. The retroperitoneal balloon dissector (Origin Systems, Inc.) was placed and the balloon inflated. This assisted the surgeon by gently pulling the posterior peritoneum away from the psoas. When the balloon has achieved maximum inflation it was removed the retroperitoneal space inflated with carbon dioxide. The next portal was placed in the mid axillary line over the inferior adjacent vertebra. Blunt dissection was then used to develop the retroperitoneal space. As the dissection is carried cephalad the next portal was placed in the anterior axillary line over the site of pathology. The endoscope was switched to that portal to complete the dissection.

Once the inferior adjacent vertebra was identified, its segmental vessels were clipped, cauterized and divided. Likewise, the segmental vessels at the site of pathology were divided allowing the surgeon to retract the great vessels anteriorly. The crux of the diaphragm is found overlying the vertebrae cephalad to L2. It was elevated subperiosteally to allow fall visualization of the cephalad adjacent vertebra. The attachments of the psoas were also elevated subperiosteally using Cobb elevators and electocautery.

Placement of the cephalad portal in the mid axillary line over the superior adjacent vertebra is more difficult. If the portal lies cephalad to the $12^{th}$ rib, care must be taken not to injure the lung at the time of insertion. Usually, we deflated the affected lung by occluding the double lumen endotracheal tube. The diaphragm is stretched cephalad up against the chest wall to push the lung out of the way and attempted to penetrate the diaphragm at its periphery. This way the portal also acted as a diaphragm retractor during the rest of the procedure. Occasionally, it is necessary to place the cephalad portal entirely within the chest cavity. In such cases, the lung is deflated and used the endoscope to ensure that the lung was retracted away from the diaphragm. Again, we attempted to penetrate the diaphragm at its periphery. Occasionally, a portal can be made in the diaphragm itself and repaired it at the end of the procedure.

The endoscope was then returned to the middle portal directly over the site of pathology.

Often the psoas must be retracted throughout the procedure. In many cases we have used a Steimann pin or a small Rush rod placed through a small stab incision to drive into the bone above and below the site of pathology in a position which retracts the psoas laterally.

Discectomy and Vertebrectomy

Disc excisions were then performed. The disc caudal to the site of pathology was addressed first through the mid axillary portal. The great vessels were retracted anteriorly. The annulus was divided using electocautery and a Cobb elevator was used to separate the cartilaginous end plate from the bony end plate. Long pituitaries, Cobb elevators, and Kerison punches were necessary. The disc was removed as completely as possible so that a Penfield could be placed through the disc space to palpate the opposite bone edge. The dissection was carried posteriorly but not up to the spinal canal. A similar discectomy was performed of the cephalad adjacent disc.

During this study, it was determined that it is extremely important to maintain orientation throughout the procedure. It is preferable to remove the entire disc so that the opposite side may be palpated to provide another visual marker.

If necessary, a vertebrectomy was then performed. The quality and position of the vertebra will dictate the method. For strong bone, we prefer to use osteotomes followed by pituitaries. In soft or fractured bone, large pituitaries are strong enough to remove most bone. Long curettes are also very useful. The bone dissection was carried through the opposite cortex.

Distraction

In cases where a kyphotic deformity is present, an endoscopic distracter was used to correct the kyphosis and left in place while the spinal canal is decompressed. A distraction device in a locked and retracted position such as described above was engaged to an insertion driver of this invention and delivered to the site. The device was placed between two vertebrae with the vertebral engagement surfaces of either end engaging the endplates of the vertebrae. The driver mechanism of the driver was actuated to engage an internal hex in the end cap of the device and push the pinion-locking member into the pinion position. The outer shaft was then rotated to turn the pinion-locking member until the rack extended to distract the vertebrae to a desired distance. The driver mechanism was then disengaged from the pinion-locking member to allow the member to return to a locked position. The distance was then measured through the cannula.

Decompression

Maintaining visual orientation is the most important part of performing spinal canal decompression. It is worth the extra time necessary to develop easily visualized landmarks which can be used to quickly check the scope orientation and depth.

The spinal canal must first be entered safely. Typically this was done through the cephalad adjacent disc by carrying the dissection posteriorly until the posterior edge of the cephalad adjacent vertebra was identified and palpated. The annulus was then pulled anteriorly using small angled curettes and small Kerison rongeurs. If there had been a burst fracture, bone fragments were individually pulled anteriorly with a curette. The pedicles of the fractured vertebral body serve to identify the lateral margins of the canal decompression. The dissection was carried caudally until the top of the caudal adjacent vertebra was reached.

Bleeding control is necessary to maintain orientation and thereby protect the neural and vascular structures. Where bone bleeding was encountered during the vertebrectomy, bone wax was used to maintain visualization and orientation. Epidural bleeding was likewise a problem in some patients and in such cases we used cottonoids and bipolar electocautery successfully.

Fusion

A bone graft was cut to the necessary length as determined by the amount of distraction between the adjacent vertebral bodies. We used either allograft tibia or autograft iliac crest at the thoracolumbar junction. The bone graft was placed endoscopically using bone holders and long impacters. The graft was placed from the inferior end plate of the cephalad vertebra to the superior end plate of the caudal vertebra.

The distracter was then returned to its retracted position and removed through the cannula.

Internal fixation was then performed either anteriorly or posteriorly, as appropriate for the patient's condition.

Post Operative

A chest tube is generally used post operatively. Even when the chest cavity was not violated, a pneumothorax can be found due to the pneumo-retroperitoneum when L1 was approached. The cephalad portal was often used for placement of the chest tube.

Although a tension pneumothorax is very unlikely with carbon dioxide; occasionally a fourteen gauge plastic intravenous cannula was placed into the chest cavity above the operated area to alleviate this concern.

ILLUSTRATIVE CASE REPORT

AK is a 65 year old woman who was the retrained drive in a single car accident. Her vehicle left the roadway, descended into a drainage ditch and came to rest in a corn field. She had immediate pain in her back, but was able to drive the car back onto the road. The next day, she sought the advice of her chiropractor who performed chiropractic treatment for 10 days. During the period, her back pain became worse and she began experiencing burning dysesthesias in both buttocks and numbness on the bottoms of her feet. She also began to have urinary incontinence. She went to her gynecologist, who sent her to an orthopaedist on the 14$^{th}$ day after her accident. At that time, she was incontinent and partially paraplegic. The orthopaedist diagnosed a L1 burst fracture with spinal cord compromise and referred her for immediate treatment.

On arrival at the emergency room, she was in extreme discomfort with any movement of her back. Her pain was primarily burning in character and located over the buttocks and posterior thighs. Tingling of the legs occurred with movement or coughing. She was unable to lie flat due to sever COPD.

She had a palpable, ender gibbus deformity at the upper lumbar spine. Neurologically, she was noted to have global weakness of all muscles of both lower extremities. There was diffuse altered sensation and tingling of both legs and she was hyper reflexic at the left knee. Clonus was evident on the left side. Rectal examination showed normal tone and preserved perianal sensation. A post void urinary residual revealed 525 cc of urine.

She also had a life long aversion to doctors and had avoided treatment for her other medical problems. These included a 10 cm parotid gland mass, severe COPD and congestive heart failure.

Radiographs revealed a Denis Type C burst fracture of L1. Computed tomography revealed extensive comminution of the fracture and 70% canal compromise. MRI showed conus medularis compression with retropulsed bone. Abnormal signal was noted in the spinal cord.

Surgical decompression was planned using the endoscopic retroperitoneal thoraco-abdominal approach, spinal cord decompression and anterior bone graft with allograft fibula. Surgical stabilization was planned using posterior fusion with instrumentation from T10 to L3.

The above-described procedure was performed anteriorly. Multiple pieces of comminuted L1 vertebral body were removed from the spinal canal. Two pieces of fibular allograft were placed between T12 and L2 after reducing the kyphotic deformity. Posteriorly she had a dual rod construct from T10 to L3 using pedicle screws/infra laminar hoods in L3, sublaminar wires at L2, T12 and T11, and a hook/claw construct at T10. Autograft was taken from the iliac crest and remaining bone from the vertebrectomy.

The anterior procedure took 230 minutes. The total duration of both anterior and posterior procedures was 550 minutes. Blood loss for the anterior procedure was 150 cc. Total blood loss was 600 cc.

She was placed in a thoraco-lumbar-sacral orthosis post operatively for five months. Post operatively, she noted immediate improvement in dysesthetic pain. Her sensation improved immediately. Bladder control returned to normal in 2 weeks. Muscle strength returned gradually so that at 6 weeks post operatively she was ambulating with a walker. By six months she had a normal motor examination. Hyper reflexia of the left knee and ankle remained permanently.

At two year follow-up she had a solid fusion both anteriorly and posteriorly. She describes her functional status as normal.

DISCUSSION

The devices and procedures of this invention were developed in an attempt to provide exposure to the thoraco lumber junction for treatment of traumatic, neoplastic, infectious processes or spinal deformities.

Other authors have reported on endoscopic retroperitoneal approaches. Southerland et al., evaluated transperitoneal and retroperitoneal approaches in the porcine model and felt that the difficulties encountered with retroperitoneal approach to the lumbar spine were significant. Their series in pigs included problems with loss of pneumoperitoneum and excessive bleeding when mobilizing the psoas muscle from the spine. They concluded that the transperitoneal approach held greater promise.

Endoscopic decompression of the spinal cord through vertebrectomy has been reported by McAfee et al., in 8 patients. There were eight cases of thoracic fracture or tumor which were treated with thoracoscopic anterior decompression. The method of surgical stabilization was not presented. Greater blood loss (avg. 1175 cc) was reported with these corpectomies compared with other endoscopic spine procedures. They illustrated one case of T12 burst fracture treated with thoracoscopic T12 vertebrectomy and posterior fusion.

Huang, et al., reported 38 patients treated with video assisted surgery at the thoraco lumbar junction. However, in their series a thoractomy was performed to accomplish the procedure. The endoscope was used to enhance visualization at the operatie site. None of their cases were fully endoscopic. They felt that the visualization allowed use of a smaller incision with less blood loss.

These reports suggest that the risk and difficulty of endoscopic retroperitoneal approach to the lumbar spine are high. A porcine laboratory model was used to develop the retroperitoneal approach technique. Endoscopic vertebrectomy, spinal cord decompression and anterior fusion are recommended in a patient only after safely accomplishing the procedure in the laboratory on several occasions.

In this case presented above the patient's pre-existing pulmonary and cardiac disease increased the risk associated with traditional tenth rib thoroco-abdominal approach. She had a long history of smoking and recent congestive heart failure. Violating the left chest carried significant risk of post operative pulmonary complications. In McAfee's series there were five patients with post thorascopy atelectasis severe enough to prolong hospitalization. One patient had persistent pleural effusion. A small chest tube is recommended as a precaution against post operative pneumothorax but the pleura was not violated surgically so we felt the overall risk is substantially reduced.

Endoscopic retroperitoneal approach to the upper lumbar spine offers significant advantageous over the traditional tenth rib thoraco-abdominal approach. In cases where thoracoscopy may be avoided, the thoracic cavity may be spared any surgical trauma. When combined with posterior fixation and fusion the endoscopic retroperitoneal approach may allow complete decompression and anterior load sharing without dramatically increasing surgical morbidity over posterior fusion only. In young patients with solid anterior vertebral bone, this approach may be combined with endoscopically placed anterior internal fixation to accomplish a one stage treatment for burst fractures with the minimum skin incision, dissection of the diaphragm, muscle damage and number of levels fused. The devices of this invention allow distraction to be accomplished endoscopically solely with the anterior approach.

The endoscopic retroperitoneal thoroco abdominal approach places severe demands on the endoscopic surgeons and equipment. The risks of blood loss and neurologic injury are present, particularly early in the learning curve. We feel that this surgical intervention should be thoroughly practiced in the animal laboratory before progressing to patients.

REFERENCES

Bradford D S, in *Moe's Textbook of Scoliosis and Other Spinal Deformities*, pp. 162–185.

Huang T J, Hsu R W W, Liu H P, Hsu K Y, Liao Y S, Shih H N, Chen Y J; "Video-Assisted Thoracoscopic Treatment of Spinal Lesions in the Thoracolumbar Junction." Surg Endosc (1997) 11:1189–1193.

McAfee P C, Regan J R, Zdeblick T, Zuckerman J, Picetti G D III, Heim S, Geis W P, Fedder I L; "The Incidence of Complications in Endoscopic Anterior Thoracolumbar Spinal Reconstructive Surgery. A Prospective Multi Center Study Comprising the First 100 Consecutive Cases." *Spine* 20 (13): 1624–32, 1995.

Southerland S R, Remedios A M, McKerrell J G, Litwin D; "Laparoscopic Approaches to the Lumbar Vertebrae. An Anatomic Study Using a Porcine Model." *Spine* 20(14) :1620–3, 1995.

Zucherman J F, Zdeblick T A, Bailey S A, Mahvi D, Hsu K Y, Kors D; "Instrumented Laparoscopic Spinal Fusion. Preliminary Result." *Spine* 20(18):2029–34, 1995.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

What is claimed:

1. A spinal distraction device, comprising:
    a body having a vertebral endplate engagement end, an opposite end and a length between said engagement end and said opposite end, said body defining
        a chamber along said length and an opening at said opposite end in communication with said chamber, and
        a gear bore at a location along said length, said gear bore in communication with said chamber and having an axis perpendicular to said length;
    a rack slidably disposed through said opening and within said chamber, said rack having
        a first end, a second end and a foot projecting transversely from said first end, said foot having a vertebral engaging surface, said rack slidable between
            a retracted position with said second end of said rack adjacent said vertebral engaging end of said body and said foot adjacent said opposite end of said body and
            a number of extended positions wherein said foot is at a distance from said opposite end of said body,
        said rack defining an engagement member between said first end and said second end, said engagement member defining an engagement surface exposed to said gear bore; and
    a pinion-locking member rotatably and slidably disposed within said gear bore, said member including
        a pinion portion defining a pinion surface complementary to said engagement surface and rotatable within said gear bore to mesh with said engagement surface to convert rotary motion of the member to reciprocating motion of the rack, and
        a locking portion at an end of said member, said locking portion preventing rotation of said member within said gear bore;

said member slidable between a pinion position in which said pinion portion is disposed within said gear bore and a locked position in which said locking portion is disposed within said gear bore.

2. The device of claim 1, further comprising:
a spring disposed in said gear bore and biasing said pinion-locking member toward said locked position.

3. The device of claim 1 wherein said engagement surface of said rack includes a number of spaced apart teeth and said pinion surface defines pinion teeth for meshing with said spaced apart teeth.

4. The device of claim 3 wherein said locking portion defines a number of locking teeth along an outer surface of said locking portion, and said body defines a locking groove at one portion of said gear bore for each said locking tooth, each said groove sized and shaped to engage one of said locking teeth to prevent rotation of said pinion-locking member when said member is in said locked position.

5. The device of claim 4 wherein said gear bore is defined through said body from a first side of said body to an opposite side of said body, said gear bore terminating at a first gear opening at said first side of said body and an opposite gear opening at said opposite side of said body, said opposite side defining said locking grooves circumscribing said opposite opening.

6. The device of claim 5, further comprising a retainer attached to said locking portion, said retainer having an outer dimension larger than a dimension of said opposite gear opening.

7. The device of claim 6, wherein
said locking portion defines a pin hole; and
said retainer includes an enlarged head defining said outer dimension and a stud extending from said head, said stud inserted into said pin hole.

8. The device of claim 5, wherein said pinion-locking member includes an end cap adjacent said pinion portion, said end cap having an outer dimension larger than a dimension of said first gear opening.

9. The device of claim 8, wherein said cap includes a tool engaging member for providing a rotational force to said pinion-locking member.

10. The device of claim 9, wherein said tool engaging member is an internal hex defined in an end of said end cap.

11. The device of claim 1, wherein said foot and said vertebral engagement end each define a vertebral endplate engaging surface.

12. The device of claim 11, wherein said vertebral engaging surfaces each include a number of ridges.

13. The device of claim 1, wherein:
an outer surface of said body defines a channel along a portion of said length, said channel in communication with said chamber; and
said rack includes a pin slidably disposed within said channel.

14. The device of claim 1, further comprising a projection extending from said body, said projection sized and shaped for grasping to position said body.

15. The device of claim 5, further comprising a projection extending from said first side of said body, said projection sized and shaped for grasping to position said body.

16. The device of claim 1, wherein an outer surface of said rack includes ruled indicia for measuring a distance between foot and said opposite end of said body when said rack is in one of said extended positions.

17. The device of claim 5, wherein said vertebral engagement end of said body and said foot of said rack each terminate in a hook.

18. The device of claim 17, wherein each said hook defines a cavity for receiving a rod, said cavities opening to said opposite side of said body.

19. The device of claim 17, wherein each said hook defines a cavity for receiving a rod, said cavities opening to said first side of said body.

20. A spinal distraction device comprising:
a pair of opposite vertebral endplate engagement feet, each having a vertebral engaging surface configured for engaging a vertebral endplate;
a rack and pinion mechanism disposed between said pair of feet and operable to vary the distance between vertebral endplates contacting said feet; and
means for locking said rack and pinion mechanism with the vertebral endplates at a fixed distance apart.

21. The spinal distraction device of claim 20, wherein said rack and pinion mechanism includes means for engaging an external tool for operating said mechanism.

22. The spinal distraction device of claim 20, further comprising:
a body integral with one of said pair of engagement feet, said body defining;
a chamber along a length thereof sized to slidably receive said rack therethrough; and
a bore intersecting said chamber;
wherein said rack and pinion mechanism includes;
a rack integral with the other of said engagement feet slidably disposed within said chamber; and
a pinion element rotatably disposed through said bore in operative engagement with said rack.

23. The spinal distraction device of claim 22, wherein said rack and pinion mechanism includes means for engaging an external tool for operating said mechanism.

24. The spinal distraction device of claim 23, wherein said means for engaging includes an internal hex defined in said pinion element sized to receive a hex end of an external tool.

25. The spinal distraction device of claim 23, wherein said means for locking is disposed between said bore and said pinion element.

26. The spinal distraction device of claim 25, wherein:
said pinion element includes;
an elongated member;
a pinion gear disposed at one end of said elongated member, said pinion gear configured to mesh with said rack; and
a number of locking teeth defined at a locking portion of said elongated member; and
said bore defines a number of locking grooves sized to receive a corresponding number of locking teeth to prevent relative rotation between said pinion element and said bore.

27. The spinal distraction device of claim 26 further comprising means for biasing said pinion element so that said locking portion is disposed within said bore.

28. The spinal distraction device of claim 27, wherein said means for biasing includes a spring disposed in said bore, whereby the spring is compressed to remove said locking portion from within said bore and to move said pinion gear into engagement with said rack.

29. The spinal distraction device of claim 20, wherein said pair of feet each define a hook configured for receiving a rod therethrough.

30. The spinal distraction device of claim 22, wherein said body defines a projection extending therefrom configured for grasping to manipulate said device.

* * * * *